US012232809B2

(12) United States Patent
Matz et al.

(10) Patent No.: US 12,232,809 B2
(45) Date of Patent: Feb. 25, 2025

(54) SYSTEM FOR PROVIDING VISUALIZATION DATA FOR VISUALIZING AT LEAST ONE SECTION OF A PATIENT'S EYE FROM OCT SCANNING DATA, AND COMPUTER-IMPLEMENTED METHOD AND COMPUTER PROGRAM (71) Applicant: Carl Zeiss Meditec AG, Jena (DE)

(72) Inventors: Holger Matz, Unterschneidheim (DE); Benjamin Sorg, Aalen (DE)

(73) Assignee: CARL ZEISS MEDITEC AG, Jena (DE)

(*) Notice: Subject to any disclaimer, the term of this patent is extended or adjusted under 35 U.S.C. 154(b) by 857 days.

(21) Appl. No.: 17/349,348

(22) Filed: Jun. 16, 2021

(65) Prior Publication Data
US 2021/0386286 A1 Dec. 16, 2021

(30) Foreign Application Priority Data
Jun. 16, 2020 (DE) .................. 10 2020 115 888.2

(51) Int. Cl.
A61B 3/10 (2006.01)
A61B 3/00 (2006.01)
(Continued)

(52) U.S. Cl.
CPC ............ *A61B 3/102* (2013.01); *A61B 3/0041* (2013.01); *A61B 90/39* (2016.02); *G06T 7/60* (2013.01);
(Continued)

(58) Field of Classification Search
CPC ......... A61B 3/02; A61B 3/102; A61B 3/1025; A61B 3/0075; A61B 3/113; A61B 3/1015; A61B 3/1225; A61B 3/024; A61B 3/005
See application file for complete search history.

(56) References Cited

U.S. PATENT DOCUMENTS 11,452,433 B2 * 9/2022 Tearney ................... A61B 1/05
2013/0242259 A1 9/2013 Hacker et al.
(Continued)

FOREIGN PATENT DOCUMENTS

DE 10 2010 046 500 A1 3/2012
EP 2427723 B1 12/2018
(Continued)

OTHER PUBLICATIONS

German Office Action for German Patent Application No. 10 2020 115 888.2, dated Mar. 16, 2021, (10 pages), the German Patent and Trade Mark Office, München, Germany.
(Continued)

Primary Examiner — Dawayne Pinkney
(74) Attorney, Agent, or Firm — Alston & Bird LLP (57) ABSTRACT Provided is to a system with an interface for providing visualization data for visualizing at least one section of a patient's eye, comprising an OCT device for capturing OCT scanning data by scanning the section of the patient's eye by means of an OCT scanning beam and comprising a computer unit for processing the OCT scanning data into the visualization data within the scope of an image rectification algorithm, which is designed to output the visualization data at the interface. The computer unit contains a view generation algorithm for calculating image data in relation to a view of a reference object arranged in the section of the patient's eye from geometry data about the reference object fed to the view generation algorithm and from the OCT scanning data obtained in relation to the reference object, wherein the computer unit has an algorithm control routine which specifies the image rectification algorithm and determines the image rectification algorithm from the image data of the view of the reference object calculated in the view generation algorithm and from OCT scanning data obtained in relation to the reference object by scanning the section of the patient's eye.

16 Claims, 5 Drawing Sheets (51) Int. Cl.
  *A61B 3/02*    (2006.01)
  *A61B 3/12*    (2006.01)
  *A61B 90/00*   (2016.01)
  *G06T 7/60*    (2017.01)

(52) U.S. Cl.
  CPC .......... *A61B 2090/3904* (2016.02); *G06T 2207/10101* (2013.01); *G06T 2207/30041* (2013.01)

(56) References Cited

U.S. PATENT DOCUMENTS

| | | | | |
|---|---|---|---|---|
| 2014/0100439 A1* | 4/2014 | Jones | .................... | G06T 7/0016 600/407 |
| 2016/0089015 A1* | 3/2016 | Eslami | ...................... | G06T 5/50 351/206 |
| 2017/0209042 A1* | 7/2017 | Matz | .................. | A61F 9/00736 |
| 2021/0137601 A1 | 5/2021 | Kindt et al. | | |

FOREIGN PATENT DOCUMENTS

| WO | WO-2015/091796 A2 | 6/2015 |
|---|---|---|
| WO | WO-2019/215061 A1 | 11/2019 |

OTHER PUBLICATIONS

Office Action for German Patent Application No. 10 2020 115 888.2, dated Mar. 16, 2021, German Patent and Trade Mark Office, München, Germany, 21 pages.

\* cited by examiner

SYSTEM FOR PROVIDING VISUALIZATION DATA FOR VISUALIZING AT LEAST ONE SECTION OF A PATIENT'S EYE FROM OCT SCANNING DATA, AND COMPUTER-IMPLEMENTED METHOD AND COMPUTER PROGRAM

CROSS-REFERENCE TO RELATED APPLICATIONS

This application claims priority to German Patent Application No. 10 2020 115 888.2, filed Jun. 16, 2020, the entire contents of which are incorporated herein by reference.

DESCRIPTION

The invention relates to a system with an interface for providing visualization data for visualizing at least one section of a patient's eye, comprising a device for capturing OCT scanning data by scanning the section of the patient's eye by means of an OCT scanning beam and comprising a computer unit for processing the OCT scanning data into the visualization data within the scope of an image rectification algorithm, which is designed to output the visualization data at the interface.

The intra-surgical optical coherence tomography (OCT) reconstruction of an optically semitransparent object, e.g., of the human eye, is dependent on the optical properties of the object during a surgical intervention. By way of example, the individual human refractive index, the current corneal curvature, injected liquids, pressure on the eye, introduced surgical instruments, natural aberrations of the eye, or other circumstances influence the optical properties of the human eye during the surgery. As a result, distortions may arise in the image reconstruction of the OCT scanning data during a surgical intervention. Therefore, the captured OCT scanning data of the patient's eye must be rectified.

OCT scanning data provide information in relation to the relative spatial position of scattering centers for the OCT scanning light in the coordinate system of the OCT system. In an OCT system, an OCT scanning beam which has been scattered back from scattering centers in the object region is made to interfere with a reference beam with a known optical path length in order thereby to allow deduction of the optical path length traversed by the OCT scanning light to a scattering center in the OCT scanning beam and back to a sensor device in the OCT scanning beam. The relative spatial position of a scattering center is then determined from the optical path length of the OCT scanning beam captured in this respect and the direction set for the latter. Since the speed of light c is different in different media, such as air and body tissue of a patient, an OCT scanning beam is generally refracted when the latter transitions from one medium into another medium, with the wavelength of the OCT scanning light also being modified. In order to determine the accurate location of scattering centers in the coordinate system of the OCT system by means of an OCT system it is therefore necessary to take account of both the refraction of the OCT scanning beam and the varying wavelength of the OCT scanning light of the OCT scanning beam in different media. If neither the refraction of the OCT scanning beam nor the change of its wavelength is taken into account, the relative spatial position of scattering centers in a scanned object region as derived from the OCT scanning data differs from the actual location of the scattering centers and hence it is distorted.

A system of the type set forth at the outset for rectifying captured OCT scanning data of a patient's eye is known from WO 2015/091796 A2. Described therein is a method which scans the corneal surface of the patient's eye by means of the OCT system and completes or reconstructs the former on the basis of model knowledge in order to consider the profile of the corneal surface when calculating the relative spatial position of scattering centers for the OCT scanning light in the interior of the patient's eye. The OCT scanning data are rectified on the basis of the curve of this reconstructed corneal surface.

EP 2 427 723 B1 has disclosed a method for rectifying OCT scanning data, which determines refraction surfaces and the curvature or normal vectors within a sample in a first step and ascertains iteratively corrected positions of the voxels in the OCT volume in a second step on the basis of the direction of incidence of the light, the ascertained normal vectors, and the refractive index of the sample.

It is an object of the invention to specify an alternative system for rectifying OCT scanning data of a patient's eye.

This object is achieved by the system specified in claim 1, the method specified in claim 7, and the computer program specified in claim 15. Advantageous embodiments and developments of the invention are specified in the dependent claims.

The system according to the invention specified in claim 1 contains an interface for providing visualization data for visualizing at least one section of a patient's eye and also a device for capturing OCT scanning data by scanning the section of the patient's eye by means of an OCT scanning beam and a computer unit for processing the OCT scanning data into the visualization data within the scope of an image rectification algorithm, which is designed to output the visualization data at the interface. In this case, the computer unit contains a view generation algorithm for calculating image data in relation to a view of a reference object arranged in the section of the patient's eye from geometry data about the reference object fed to the view generation algorithm and from the OCT scanning data obtained in relation to the reference object, wherein the computer unit has an algorithm control routine which specifies the image rectification algorithm and determines the image rectification algorithm from the image data of the view of the reference object calculated in the view generation algorithm and from OCT scanning data obtained in relation to the reference object by scanning the section of the patient's eye.

Within the scope of the invention, a reference object is understood to be an object arranged in the section of the patient's eye, e.g., surgery instruments or implants.

Within the scope of the invention, geometry data about the reference object are understood to be data which describe the 3D geometry of the reference object, e.g., CAD data or a 3D reconstruction of the reference object.

The inventors have recognized that the captured OCT scanning data can be rectified if a reference object with known or ascertainable geometry data is arranged in the section of the patient's eye. An image rectification algorithm for the OCT scanning data can be ascertained on the basis of the geometry data about the reference object and the image representation of the reference object in the captured OCT scanning data. To this end, a view of the reference object without distortions, which is as similar as possible to the image representation of the reference object in the OCT scanning data, is generated from the geometry data. Then, a rectification mapping is ascertained, which maps the image representation of the reference object in the distorted OCT scanning data onto the undistorted view of the reference object. This rectification mapping only relates to points of the reference object in the OCT scanning data and is therefore extrapolated to points outside of the reference object, in particular points in the vicinity of the reference object, in the OCT scanning data. Then, the image rectification algorithm consists in applying the extrapolated rectification function to the captured OCT scanning data.

It should be noted that both the view of the reference object generated on the basis of the geometry data and the image representation of the reference object in the OCT scanning data can be two-dimensional or three-dimensional.

In this case, it is advantageous that at least one marker that is able to be captured by scanning by means of an OCT scanning beam is attached to the reference object. In particular, the marker is embodied as an identification marker in this case, which contains information able to be captured by scanning by means of an OCT scanning beam and relating to the type of reference object, and which serves to identify the reference object. Furthermore, it is advantageous if the marker is embodied as a geometric marker which contains information able to be captured by scanning by means of an OCT scanning beam and relating to the geometry of the reference object. Moreover, it is advantageous if the marker defines a coordinate system, the location of which can be captured by scanning the marker by means of an OCT scanning beam. Attaching markers to the reference object is advantageous in that the type of reference object, the geometry of the reference object, and/or the position and location of the reference object can be determined more easily, with less outlay and with greater accuracy.

The system for providing visualization data for visualizing at least one section of a patient's eye can also contain a measuring unit, which ascertains the position and location of the reference object in the section of the patient's eye and feeds these to the view generation algorithm.

The system for providing visualization data for visualizing at least one section of a patient's eye can also contain a control unit, which automatically controls the reference object in the section of the patient's eye and feeds the position and location of the reference object in the section of the patient's eye to the view generation algorithm.

Both the measuring system and the control unit are advantageous in that the position and location of the reference object can be ascertained, or are known, with a particularly high accuracy. The view of the reference object can be generated more easily and particularly accurately in the view generation algorithm on the basis of this information since there is no need for algorithms that fit the view of the reference object to the image representation of the reference object in the captured distorted OCT scanning data. This is because this step is afflicted with errors on account of the distorted OCT scanning data.

The interface is preferably embodied as a display which is designed for the visualization of the at least one section of the patient's eye.

The computer unit can contain a refractive index ascertainment routine which is designed to ascertain the refractive index of a medium arranged in the section of the patient's eye from the visualization data and from at least one dimension of the reference object. To this end, an object structure of the reference object with a known dimension $L_{Air}$ in air, for example the length of a side of an implant or of a handle section of a surgical instrument, is ascertained in the rectified visualization data and the dimension $L_{Medium}$ thereof is measured there. The refractive index of the medium $n_{medium}$ can then be ascertained as follows:

$$n_{Medium} = \frac{L_{Medium}}{L_{Air}}$$

Ascertaining the refractive index is advantageous in that additional information about the medium in the section of the patient's eye can be ascertained, which information can be used for further purposes, for example calculating a course of optical imaging beam paths in the patient's eye.

Preferably, the computer unit contains a distance ascertainment routine which serves to measure a distance between at least two points arranged in the section of the patient's eye by determining the geometric distance of an image of the at least two points in the visualization data of the section of the patient's eye. An advantage of this measure is that distances between two points in the section of the patient's eye can be determined with greater accuracy than in the distorted data.

The invention moreover relates to a computer-implemented method for providing visualization data for visualizing at least one section of a patient's eye, in which OCT scanning data are captured by scanning the section of the patient's eye by means of an OCT scanning beam and in which OCT scanning data are processed into the visualization data in an image rectification algorithm. For the purposes of calculating image data in relation to a reference object arranged in the section of the patient's eye, image data of a view of the reference object are calculated here in a view generation algorithm from geometry data about the reference object and from the OCT scanning data obtained in relation to the reference object. The image rectification algorithm is then determined from the image data of the view of the reference object calculated in the view generation algorithm and from the OCT scanning data obtained in relation to the reference object.

The type of reference object dealt with is ascertained in a first step on the basis of the captured OCT scanning data of the reference object. By way of example, this can be implemented by user inputs or else also automatically by means of known object recognition methods from the field of image processing or machine learning. Geometry data can then be ascertained in relation to the reference object, for example on the basis of a database which stores geometry data for different types of surgical instruments and implants.

As an alternative or else in addition thereto, the view generation algorithm can ascertain geometry data of the reference object by virtue of capturing OCT scanning data of the reference object in various recording positions outside of the section of the patient's eye and the geometry data of the reference object being ascertained from these OCT scanning data by means of a 3D reconstruction method. Such 3D reconstruction methods can be based on image processing or machine learning. By way of example, these are described in chapter 17 of the book "R. Hartley and A. Zisserman, Multiple View Geometry, Cambridge University Press".

Preferably, the view generation algorithm generates a view of the reference object which corresponds to the image representation of the reference object in the OCT scanning data obtained in relation to the reference object. An undistorted view of the reference object, which can be used to determine the image rectification algorithm, is ascertained in this way. To generate a view of the reference object which corresponds to the image representation of the reference object in the captured OCT scanning data, i.e., which is as similar as possible to this image representation, use can be made of methods from image processing or machine learning, for example so-called matching methods. Matching methods can serve to determine a position and location in relation to the geometry data of the reference object with respect to the OCT device such that the view of the reference object aligned on the basis of these data corresponds as accurately as possible to the 3D image representation of the reference object in the captured OCT scanning data. Alternatively, a projection of the geometry data of the reference object on a 2D image plane can also be ascertained by means of a matching method such that the projection corresponds as accurately as possible to a 2D image representation of the reference object in the captured OCT scanning data. Segmentation methods can be used to ascertain the image representation of the reference object in the captured OCT scanning data. Likewise, it is possible to use machine learning methods in order to ascertain a mapping that is as accurate as possible of the geometry data onto a 3D or 2D image representation of the reference object in the captured OCT scanning data. In this case, machine learning methods can also incorporate additional information, for example the type of reference object or the imaging properties of the OCT device. The view generation algorithm can also use user inputs, said user for example aligning the geometry data of the reference object by means of translation, rotation, and scaling in such a way that the view of the reference object (or else the 2D projection of the reference object) corresponds as accurately as possible to the 3D or 2D image representation of the reference object in the captured OCT scanning data.

Advantageously, the view generation algorithm consequently uses an image processing method and/or machine learning method in order to ascertain the geometry data in relation to the reference object and/or in order to generate the view of the reference object from the geometry data. As a result, the method can run automatically.

Preferably, the view generation algorithm in this case uses data relating to the position and location of the reference object in the section of the patient's eye for generating the view of the reference object, which are generated by a measurement method or by a control unit for automatically controlling the reference object. An advantage arising from the position and location of the reference object in the section of the patient's eye being known is that the view generation algorithm can directly generate the view of the reference object on the basis of the geometry data and the position and location of the reference object, without needing to estimate the position and location by means of an algorithm. As a result, a greater accuracy of the view of the reference object generated, and hence also of the image rectification algorithm, is achieved.

Within the scope of the invention, an image rectification algorithm is understood to be an algorithm in the form of a computation rule, which determines rectified OCT scanning data from the captured OCT scanning data, with the influences of the refraction and path length change of an OCT scanning beam, as are possible in a patient's eye, on the captured OCT scanning data being at least partly corrected.

Preferably, the image rectification algorithm determines a rectification mapping from the OCT scanning data captured by scanning the section of the patient's eye onto the visualization data. This rectification mapping represents a function $f(x)=y$, which assigns a 3D point y in the rectified visualization data to the individual 3D points x in the captured distorted OCT scanning data. Here, the function f can be formed as a parametric model, the parameters of which are ascertained on the basis of sample assignments $x \rightarrow y$ by means of parameter optimization methods, e.g., least-squares algorithms.

Preferably, the rectification mapping of the image rectification algorithm is determined by means of two method steps: In a first step, a mapping of the view of the reference object generated in the view generation algorithm onto the image representation of the reference object in the OCT scanning data obtained in relation to the reference object is ascertained. In this case, the view of the reference object generated in the view generation algorithm corresponds—apart from inaccuracies when generating the view—to a rectified representation of the reference object. The image representation of the reference object in the OCT scanning data obtained in relation to the reference object is preferably determined by means of a segmentation method, which can be based on image processing or machine learning algorithms. Alternatively, a user can also mark the image representation of the reference object in the OCT scanning data. In a second step, the ascertained mapping is then extrapolated to points of the captured OCT scanning data of the section of the patient's eye outside of the reference object.

The image rectification algorithm can also use other known methods for image rectification, as described, for example, in the book "Blind Deconvolution, Subhasis Chaudhuri, Rajbabu Velmurugan, Renu Rameshan, Springer Verlag, 2014", which is referred to herewith and the disclosure of which in chapters 3 to 7 is incorporated in this description of the invention.

In this case, the image rectification algorithm advantageously only rectifies a portion of the captured OCT scanning data, in particular the OCT scanning data in the vicinity of the reference object, with the remaining OCT scanning data remaining unchanged. This is advantageous in that a greater accuracy of the image rectification algorithm is achieved because the optical properties in the section of the patient's eye vary locally and because the assumption can be made that the image rectification algorithm determined on the basis of the reference object only fits to the regions of the section of the patient's eye in the vicinity of the reference object.

So that the image rectification algorithm reliably rectifies relatively large regions of the section of the patient's eye, it is advantageous to move a reference object through a plurality of partial sections of the section of the patient's eye and to determine visualization data using an above-described method for each of these partial sections in the captured OCT scanning data.

Since, moreover, the optical properties in the section of the patient's eye change during the surgery, it is advantageous if the visualization data are redetermined at intervals and/or depending on an event in the section of the patient's eye and/or following a user request, using an above-described method. By way of example, it is helpful to ascertain an image rectification algorithm for the captured OCT scanning data at the start of the surgery in order, for example, to take account of natural aberrations of the eye or of the corneal curvature. If a liquid is injected into the section of the patient's eye during the course of the surgery, it is necessary to ascertain a new image rectification algorithm which considers the refractive index that has been altered by the liquid. The image rectification algorithm for the section of the patient's eye can be ascertained again at intervals in automated fashion; however, it may also be ascertained again following a user request if the quality of the rectified OCT scanning data is no longer sufficient. Alternatively, an event recognition algorithm can also be used, the latter analyzing the recorded OCT scanning data or data recorded using an image capturing device during surgery and automatically triggering a re-ascertainment of the image rectification algorithm when an event is recognized, for example, when a liquid is injected or a surgical instrument is introduced or removed.

Finally, the invention also relates to a computer program product comprising a computer program having program code for carrying out all method steps which are specified in a method as presented above when the computer program is loaded on a computer unit and/or executed on a computer unit.

Below, advantageous exemplary embodiments of the invention, which are schematically depicted in the drawings, are described.

In detail.

Figure 1:
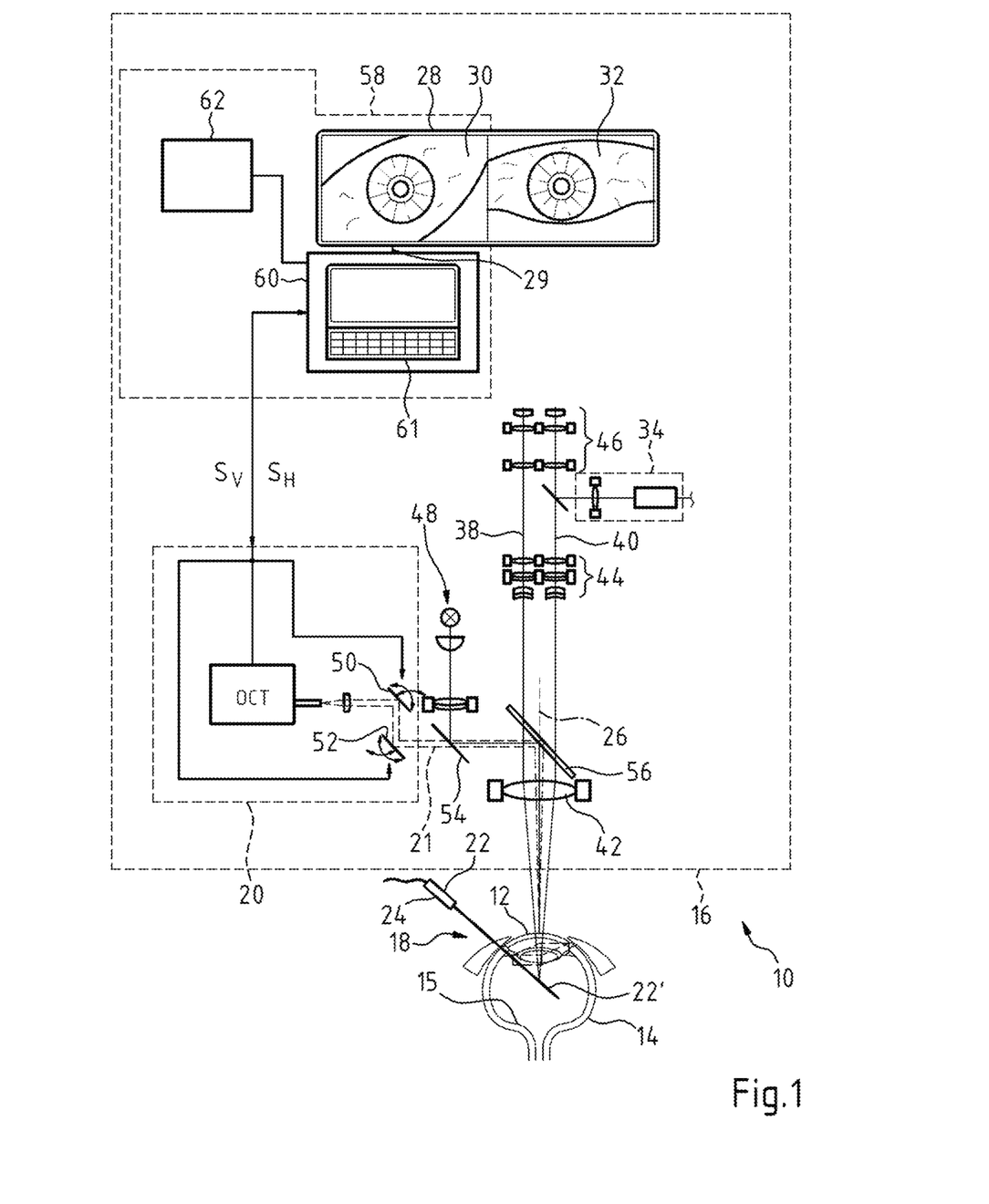
FIG. 1 shows a first system with a surgical microscope, with an OCT device for scanning a section of a patient's eye, and with a reference object in the form of a surgical instrument therein.

The system 10 shown in FIG. 1 contains a surgical microscope 16 for visualizing the section 18 of the patient's eye 14 with magnification. By way of example, the surgical microscope 16 can be the OPMI® Lumera 660. Rescan surgical microscope by Carl Zeiss Meditec AG. The system 10 comprises an OCT device 20 which provides an OCT scanning beam 21 for scanning the section 18 of the patient's eye 14 with an A-, B- and C-scan, as described, e.g., in chapter 3, pages 45 to 82 in A. Ehnes, "Entwicklung eines Schichtsegmentierungsalgorithmus zur automatischen Analyse von individuellen Netzhautschichten in optischen Kohärenztomographie—B-Scans", Dissertation, University of Giessen (2013).

The system 10 comprises a reference object 24 embodied as a surgical instrument, which, on the basis of a marker 22', is identifiable and localizable in the section 18 of the patient's eye 14 by means of the OCT device 20. An additional marker 22 can be arranged on the reference object 24 outside of the patient's eye 14.

The surgical microscope 16 comprises a stereoscopic observation beam path 38, 40, which facilitates the examination of the patient's eye 14 through a microscope main objective 42 in the section 18 of the patient's eye 14. The surgical microscope 16 comprises a zoom system 44 and an eyepiece 46. It comprises an illumination device 48 which can illuminate the section 18 with illumination light through the microscope main objective 42 for the purposes of stereoscopically visualizing the patient's eye 14 in the eyepiece 46.

The OCT device 20 provides the OCT scanning beam 21 with short coherent light, which is guided through the microscope main objective 42 to the section 18 of the patient's eye 14 by way of adjustable scanning mirrors 50, 52 and beam splitters 54 and 56. The light of the OCT scanning beam 21 scattered in the section 18 returns at least in part to the OCT device 20 via the same beam path. Then, the optical path length of the scanning light is compared in the OCT device 20 to the optical path length of a reference path. Using this, it is possible to capture the precise location of scattering centers in the section 18, in particular the position of optically effective areas, with an accuracy which corresponds to the coherence length $l_c$ of the short coherent light in the OCT scanning beam 21.

On account of refraction and path length changes of the OCT scanning beam in the patient's eye, errors may arise when determining the location of the scattering centers in the section 18 of the patient's eye 14, which are visible as distortions in the captured OCT scanning data. As a matter of principle, these aberrations are not time-invariant since the optical properties of a patient's eye 14 can change during surgery.

In the surgical microscope 16, there is a device 58 for controlling the OCT scanning beam 21 and for setting the position of the section 18 of the patient's eye 14 scanned by the OCT scanning beam 21. The device 58 contains a computer unit 60. The computer unit 60 has an input interface 61 as a means for entering information and commands by a user and contains a computer program for controlling the OCT scanning beam 21 and adjusting the spatial extent and position, i.e. the location and orientation, of the section 18 of the patient's eye 14 scanned by the OCT scanning beam 21. In this case, the device 58 for controlling the OCT scanning beam 21 is embodied for successive continuous scanning of the section 18 and of the region of the section 18 of the patient's eye 14 containing the reference object 24 by means of the OCT scanning beam 21. In this case, the OCT scanning beam 21 has a frame rate of 10 ms to 20 ms in order to allow the surgeon to have fast hand-eye coordination.

The device 58 for controlling the OCT scanning beam 21 contains a display unit 28 which is connected to the computer unit 60 and which is in the form of a display with an interface 29 for displaying the captured distorted OCT scanning data 30 with the reference object 24 and the generated rectified visualization data 32 of the section 18 of the patient's eye 14. Moreover, in the system 10, the OCT scanning information for the OCT device 20 may be visualized for a surgeon in the eyepiece 46 of the surgical microscope 16 by means of a device for mirroring-in data 34.

Further, the computer program in the program memory of the computer unit 60 contains a control routine which specifies the reference length for the OCT scanning beam 21 and the settings of the adjustable scanning mirrors 50, 52 for scanning the section 18 of the patient's eye 14. There is a control member 62, actuatable by an operator, in the device 58 for setting the section 18 scanned by means of the OCT scanning beam 21. Moreover, the control routine contains a scanning routine for scanning the reference object 24 by way of special scanning patterns. In the process, the section 18 of the patient's eye 14 is scanned at a lower rate in comparison with the reference object 24 in order to keep the amount of data as small as possible and hence the computing time as short as possible.

The computer program in the program memory of the computer unit 60 serves to process the OCT scanning data 30 into the visualization data 32 within the scope of an image rectification algorithm 80, which is designed to output the visualization data 32 at the interface 29. The computer program moreover contains a view generation algorithm 78 for calculating image data in relation to a view 76 of a reference object 24 arranged in the section 18 of the patient's eye 14 from geometry data 74 about the reference object 24 fed to the view generation algorithm 78 and from the OCT scanning data 30 obtained in relation to the reference object 24. In this case, the computer unit 60 has an algorithm control routine which specifies the image rectification algorithm 80 and determines the image rectification algorithm 80 from the image data of the view 76 of the reference object 24 calculated in the view generation algorithm 78 and from OCT scanning data 30 obtained in relation to the reference object 24 by scanning the section 18 of the patient's eye 14.

Figure 2A:
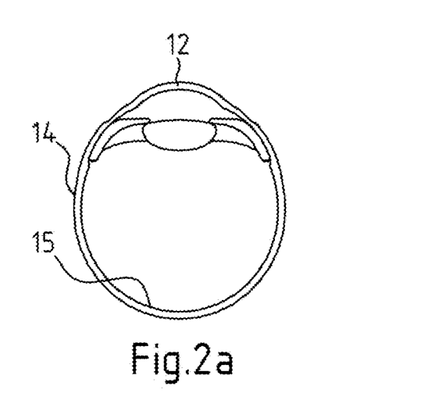
FIG. 2A shows a patient's eye.
Figure 2B:
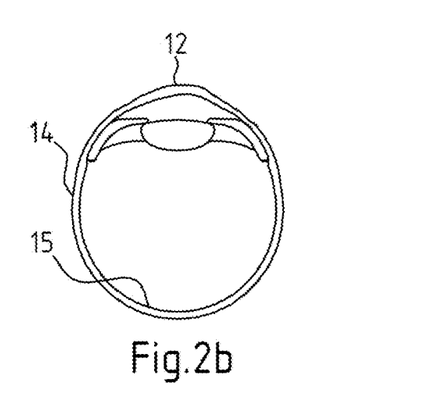
FIG. 2B shows a change in the optical properties of the patient's eye of FIG. 2A as a result of pressure from the outside.
Figure 3:
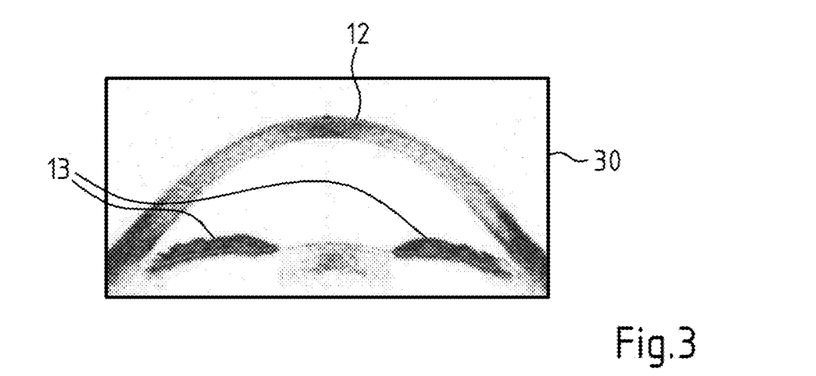
FIG. 3 shows distorted OCT scanning data of an anterior chamber of eyeball.
Figure 4:
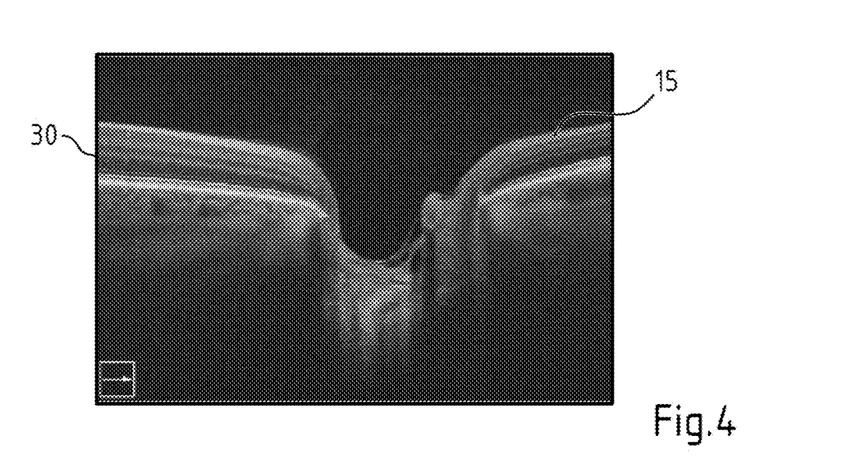
FIG. 4 shows distorted OCT scanning data of a posterior chamber of eyeball.

FIG. 2A shows a view of a patient's eye 14 with a cornea 12 and a retina 15. As a result of pressure on the patient's eye 14, the shape and the curvature of the cornea 12 changes in FIG. 2B, and so there is also change in the optical properties of the patient's eye 14. This leads to distortions in the captured OCT scanning data 30, as can be seen in FIG. 3 and FIG. 4. FIG. 3 shows distorted OCT scanning data 30 of an anterior chamber of eyeball with a cornea 12 and an iris 13. FIG. 4 shows distorted OCT scanning data 30 of a posterior chamber of eyeball with a section of the retina 15. Both OCT scanning data 30 of the anterior chamber of the eyeball and OCT scanning data 30 of the posterior chamber of the eyeball can be rectified by means of the image rectification algorithm 80.

Figure 5:
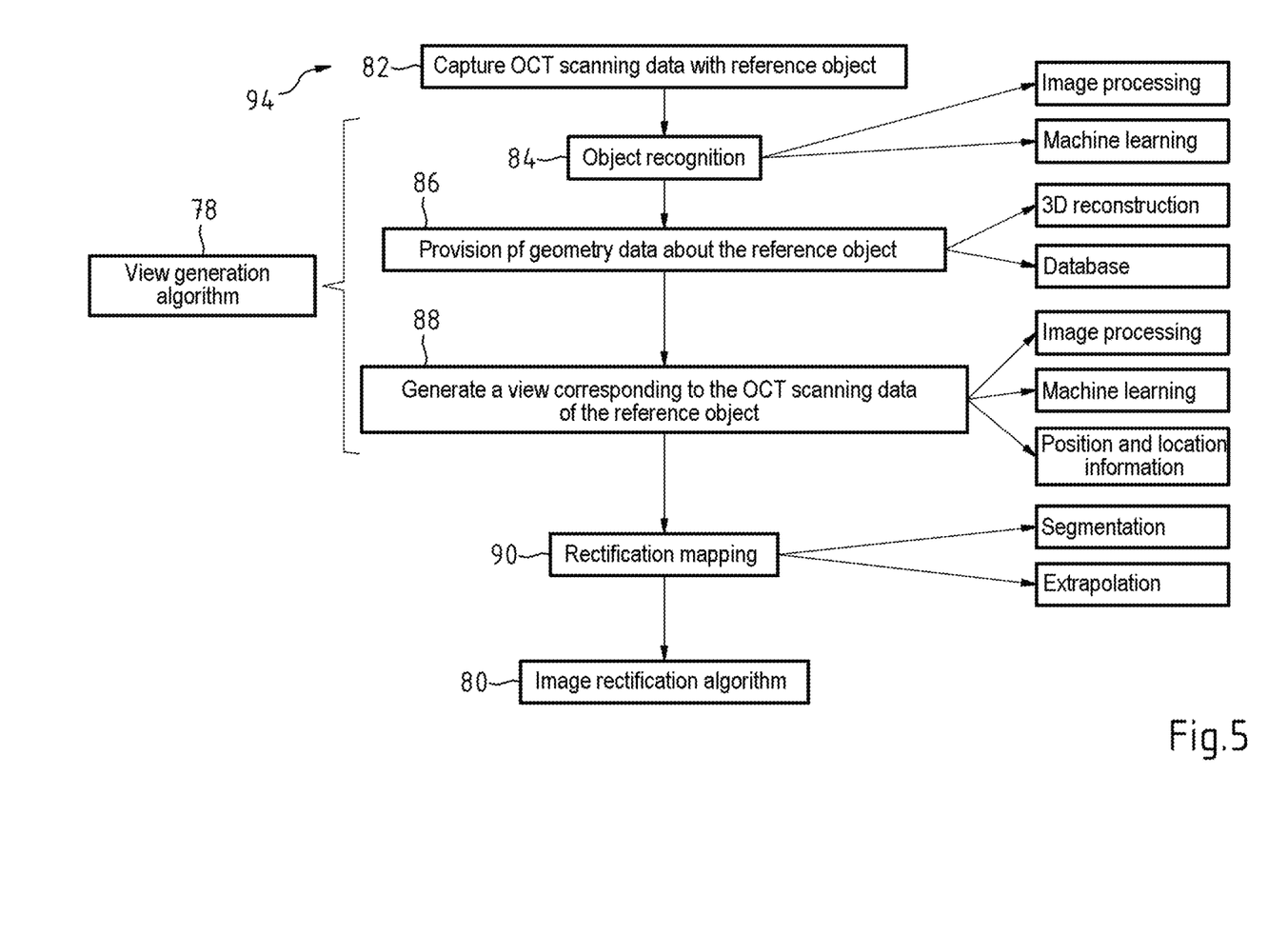
FIG. 5 shows a flowchart of one embodiment variant of the computer-implemented method.

FIG. 5 shows a flowchart for one embodiment variant of the computer-implemented method. Here, OCT scanning data 30 of the section 18 of the patient's eye 14 with a reference object 24 arranged therein are captured in a data capture step 82. These OCT scanning data 30 form the input for the view generation algorithm 78. In an object recognition step 84, the type of reference object 24 is recognized first within the view generation algorithm 78. In the present case, the type of reference object is understood to mean, for example, the use of the surgical instrument or the type of an implant arranged in the section 18 of the patient's eye 14. In this case, the object recognition step 84 can be carried out by means of image processing or machine learning on the basis of the OCT scanning data 30. Then, geometry data 74 in relation to the reference object 24 are loaded from a database, for example in the form of a CAD data record, on the basis of the type of reference object 24 within the scope of a geometry data provision step 86. Alternatively, the reference object 24 can also be moved outside of the eye while OCT scanning data of the reference object 24 are captured. Then, the geometry data 74 of the reference object 24 can be ascertained by means of a 3D reconstruction method. A view 76 of the reference object 24 is generated in a view generation step 88, which view corresponds as accurately as possible to the image representation 75 of the reference object 24 in the OCT scanning data 30. Image processing algorithms or, as an alternative or in addition thereto, machine learning algorithms, for example matching methods, are used for this purpose. If the position and location of the reference object 24 are known relative to the OCT device 20, for example on account of measurement using a measuring device, by recognizing markers 22, 22' or by way of a robotic guide of the reference object 24, it is possible to directly ascertain a suitable view 76 of the reference object 24 from the geometry data 74 and the known position and location of the reference object 24. The output of the view generation algorithm 78 consists of the view 76 of the reference object 24 generated from the geometry data 74. Now, the image rectification algorithm 80 is ascertained from the generated view 76 and the captured OCT scanning data 30, for example by determining a rectification mapping 77 in a rectification mapping determination step 90. In this case, a segmentation of the reference object 24 can be ascertained in the OCT scanning data 30 within the scope of a first step. Then, the rectification mapping 77 is determined on the basis of an image processing or machine learning method, by virtue of ascertaining the corresponding points of the reference object 24 in the generated view 76 of the reference object for points of the reference object 24 in the OCT scanning data 30. Preferably, prominent points can be chosen here, for example edges and corners, in order to achieve matching that is as accurate as possible. The point correspondences define a mapping between the image representation 75 of the reference object 24 in the captured OCT scanning data 30 and the reference object 24 in the generated view 76 of the reference object 24. Then, the rectification mapping 77 restricted to the points of the reference object 24 is determined from the point correspondences, for example by parameter estimation or by solving an optimization problem or by extrapolating the individual point correspondences to the neighboring points within the reference object 24. In order also to rectify the OCT scanning data 30 outside of the reference object 24, the rectification mapping 77 is defined for points arranged in the vicinity of the reference object 24 by means of an extrapolation 79. Points whose distance from the reference object 24 exceeds a threshold can likewise be rectified by the extrapolation 79, or they remain unchanged. The image rectification algorithm 80 generated in this way applies the rectification mapping 77 to the captured OCT scanning data 30 in an image rectification step 92 and thereby generates rectified visualization data 32, which are output on the interface 29.

On the basis of the visualization data 32, rectified OCT scanning data 30 can be displayed to a surgeon during the surgery. The visualization data 32 can also be used to measure distances between points in the section 18 of the patient's eye 14 with a greater accuracy. Finally, the visualization data 32 can also be used to determine a refractive index of a medium in the section 18 of the patient's eye 14.

Figure 6:
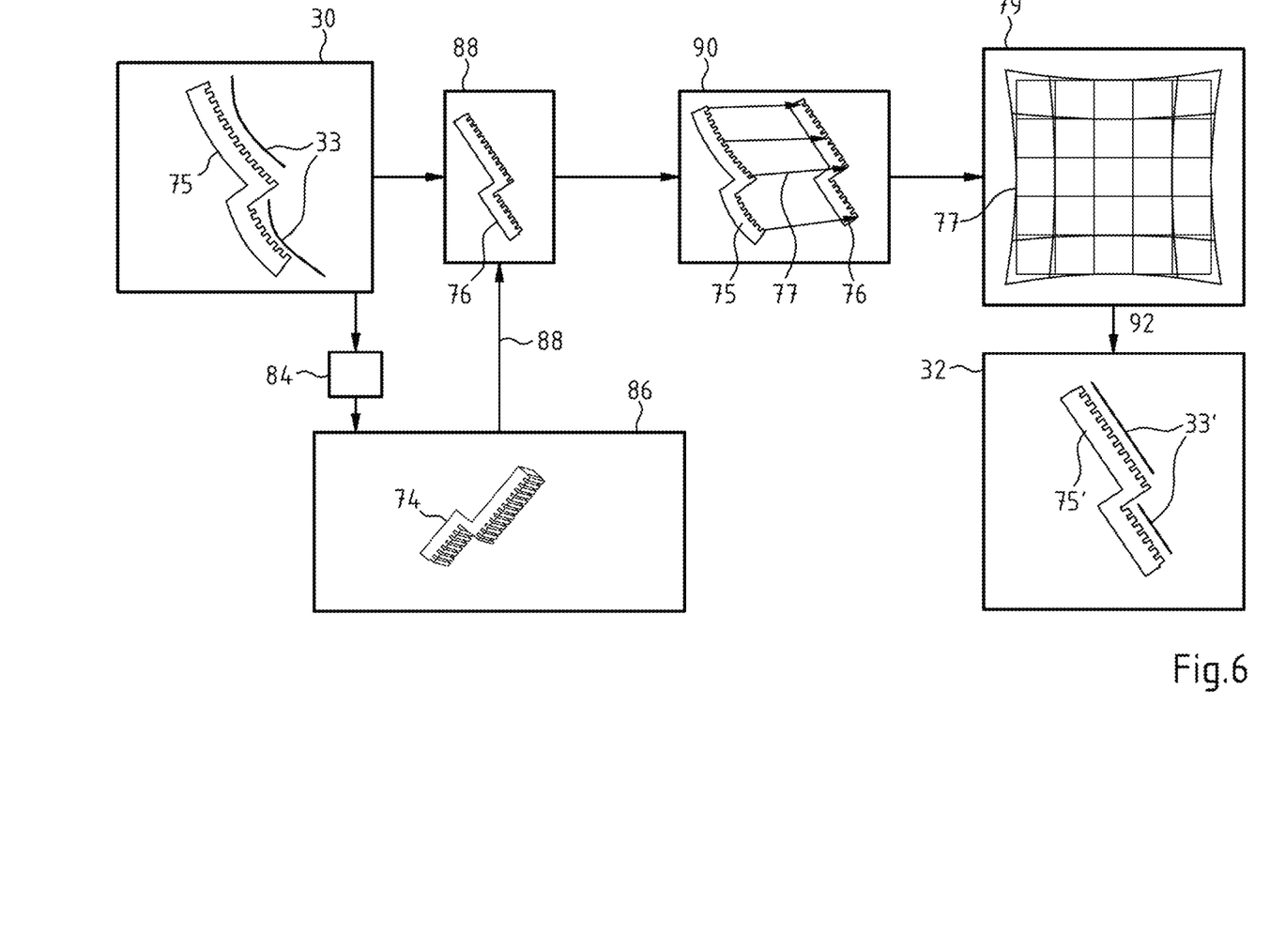
FIG. 6 shows processing steps of the captured OCT scanning data when determining the image rectification algorithm and the visualization data.

FIG. 6 shows the processing steps of the captured OCT scanning data 30 when determining the image rectification algorithm 80 and the visualization data 32. The distorted OCT scanning data 30 contain an image representation 75 of the reference object 24 and further distorted structures 33 outside of the image representation 75 of the reference object 24 in the section 18 of the patient's eye 14. The type of reference object 24 is ascertained by means of object recognition in an object recognition step 84, and the geometry data 74 in relation to this reference object 24 are generated. Then, a view 76 of the reference object 24, which corresponds as accurately as possible to the reference object 24 in the captured OCT scanning data 30, is generated in a view generation step 88 from the captured OCT scanning data 30 of the reference object 24 and from the geometry data 74 in relation to the reference object 24. No complete correspondence of the two views 76 is possible on account of the distortions in the OCT scanning data 30. In this case, the generated view 76 of the reference object 24 can be three-dimensional or two-dimensional. By way of example, a projection of the geometry data 74 can be determined for a two-dimensional view 76. Then, the image representation 75 of the reference object in the OCT scanning data 30 is ascertained first by means of segmentation or marking within the scope of a rectification mapping determination step 90 and then a rectification mapping 77 is determined, which maps points of the image representation 75 of the reference object 24 onto points of the previously generated view 76 of the reference object 24. The rectification mapping 77 is also extrapolated to the points of the OCT scanning data 30 in the vicinity of the reference object 24. This rectification mapping 77 forms the image rectification algorithm 80, which is applied to the OCT scanning data 30 in an image rectification step 92. As a result, both the image representation 75 of the reference object 24 and the further structures 33 in the OCT scanning data 30 are rectified. The result of the image rectification algorithm 80 are the visualization data 32, which contain a rectified image representation 75' of the reference object 24 and rectified structures 33' of the OCT scanning data 30 in the vicinity of the reference object 24.

Figure 7:
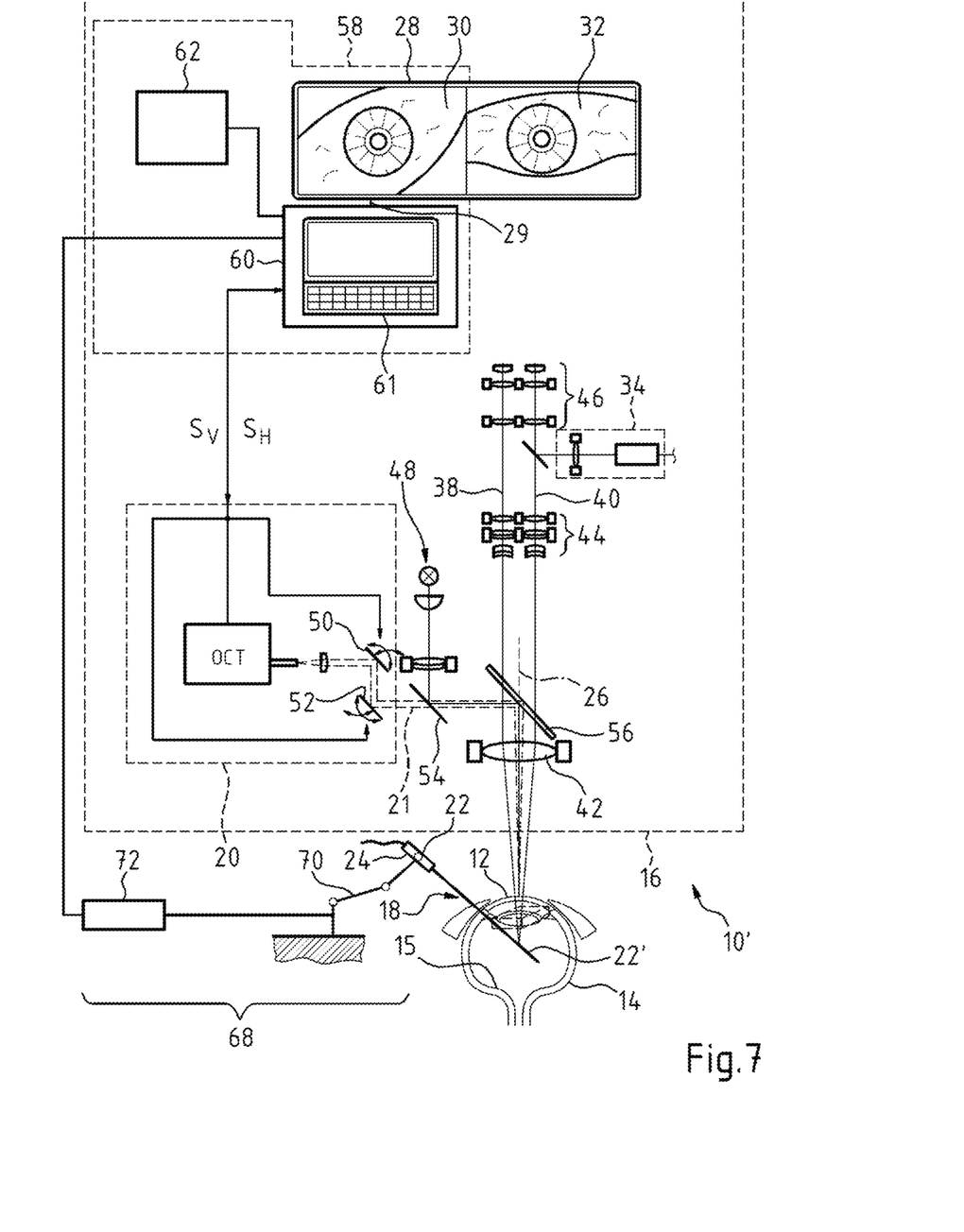
FIG. 7 shows a second system with a surgical microscope, with an OCT device for scanning a section of a patient's eye, with a reference object in the form of a surgical instrument therein, and with a control unit for controlling the reference object.

FIG. 7 shows a further system 10' with a surgical microscope 16, with an OCT device 20 for scanning a section 18 of a patient's eye 14, with a reference object 24 in the form of a surgical instrument, and with a robotics unit 68. To the extent that the components and elements of the further system 10' shown in FIG. 7 correspond to the components and elements of the first system 10 visible in FIG. 1, these have been identified with the same numerals as reference signs.

The robotics unit 68 comprises a micro robot 70 with a control unit 72. By way of example, the micro robot 70 can be embodied as a manipulator for surgical instruments with motor drives, as provided in the ophthalmic surgical operating system R1.1 by Preceyes B.V.

To ensure automation of surgery to the greatest possible extent, a movement of the reference object 24 embodied as a surgical instrument here is set by means of the micro robot 70. The micro robot 70 of the robotics unit 68 is controlled in this case on the basis of the information items processed by the computer unit 60.

On the basis of the control commands in the micro robot 70, the position and location of the reference object 24 in the form of a surgical instrument is known. This simplifies generating the view 76 of the reference object 24.

To sum up, the following preferred features of the invention should be noted: A system 10, 10' comprises an interface 29 for providing visualization data 32 for visualizing at least one section 18 of a patient's eye 14 and comprises an OCT device 20 for capturing OCT scanning data 30 by scanning the section 18 of the patient's eye 14 by means of an OCT scanning beam 21. In the system 10, 10', there is a computer unit 60 for processing the OCT scanning data 30 into the visualization data 32 within the scope of an image rectification algorithm 80, which is designed to output the visualization data 32 at the interface 29. The computer unit 60 contains a view generation algorithm 78 for calculating image data in relation to a view 76 of a reference object 24 arranged in the section 18 of the patient's eye 14 from geometry data 74 about the reference object 24 fed to the view generation algorithm 78 and from the OCT scanning data 30 obtained in relation to the reference object 24. In the computer unit 60, there is an algorithm control routine which specifies the image rectification algorithm 80 and determines the image rectification algorithm 80 from the image data of the view 76 of the reference object 24 calculated in the view generation algorithm 78 and from OCT scanning data 30 obtained in relation to the reference object 24 by scanning the section 18 of the patient's eye 14.

LIST OF REFERENCE SIGNS 10, 10' System
12 Cornea
13 Iris
14 Patient's eye
15 Retina
16 Surgical microscope
18 Section
20 OCT device
21 OCT scanning beam
22, 22' Marker
24 Reference object
28 Display unit
29 Interface
30 OCT scanning data
32 Visualization data
33 Structures
33' Rectified structures
34 Mirroring-in data
38, 40 Stereoscopic observation beam path
42 Microscope main objective
44 Zoom system
46 Eyepiece
48 Illumination device
50, 52 Scanning mirror
54, 56 Beam splitter
58 Device
60 Computer unit
61 Input interface
62 Control member
68 Robotics unit
70 Micro robot
72 Control unit
74 Geometry data
75 Image representation
75' Rectified image representation
76 View
77 Rectification mapping
78 View generation algorithm
79 Extrapolation
80 Image rectification algorithm
82 Data capture step
84 Object recognition step
86 Geometry data provision step
88 View generation step
90 Rectification mapping determination step
92 Image rectification step
94 Computer-implemented method

The invention claimed is:

1. A system with an interface for providing visualization data for visualizing at least one section of a patient's eye, comprising an OCT device for capturing OCT scanning data by scanning the section of the patient's eye by means of an OCT scanning beam and
comprising a computer unit for processing the OCT scanning data into the visualization data within the scope of an image rectification algorithm, which is designed to output the visualization data at the interface,
wherein the computer unit contains a view generation algorithm for calculating image data in relation to a view of a reference object arranged in the section of the patient's eye from geometry data about the reference object fed to the view generation algorithm and from the OCT scanning data obtained in relation to the reference object, and
wherein the computer unit has an algorithm control routine which specifies the image rectification algorithm and determines the image rectification algorithm from the image data of the view of the reference object calculated in the view generation algorithm and from OCT scanning data obtained in relation to the reference object by scanning the section of the patient's eye, said image rectification algorithm determining a rectification mapping which maps points of an image representation of the reference object in the OCT scanning data onto points of a generated view of the reference object which is based on image data calculated in relation to a view of a reference object arranged in the section of the patient's eye from geometry data about the reference object and which are fed to the view generation algorithm.

2. The system as claimed in claim 1, wherein at least one marker that is able to be captured by scanning by means of an OCT scanning beam is attached to the reference object.

3. The system as claimed in claim 2, wherein the marker is embodied as an identification marker which contains information able to be captured by scanning by means of an OCT scanning beam and relating to the type of reference object, said information serving to identify the reference object, and/or wherein the marker is embodied as a geometric marker which contains information able to be captured by scanning by means of an OCT scanning beam and relating to the geometry of the reference object and/or wherein the marker defines a coordinate system, the location of which can be captured by scanning the marker by means of an OCT scanning beam.

4. The system as claimed in claim 1, characterized by a measuring unit which ascertains the position and location of the reference object in the section of the patient's eye and feeds these to the view generation algorithm and/or by a control unit which automatically controls the reference object in the section of the patient's eye and feeds the position and location of the reference object in the section of the patient's eye to the view generation algorithm.

5. The system as claimed in claim 1, wherein the computer unit contains a refractive index ascertainment routine which is designed to ascertain the refractive index of a medium arranged in the section of the patient's eye from the visualization data and from at least one dimension of the reference object.

6. The system as claimed in claim 1, wherein the computer unit contains a distance ascertainment routine which serves to measure a distance between at least two points arranged in the section of the patient's eye by determining the geometric distance of an image of the at least two points in the visualization data of the section of the patient's eye.

7. A computer-implemented method for providing visualization data for visualizing at least one section of a patient's eye,
in which OCT scanning data are captured by scanning the section of the patient's eye by means of an OCT scanning beam and
in which OCT scanning data are processed into the visualization data in an image rectification algorithm, wherein for the purposes of calculating image data in relation to a reference object arranged in the section of the patient's eye, image data of a view of the reference object are calculated in a view generation algorithm from geometry data about the reference object and from the OCT scanning data obtained in relation to the reference object, and
wherein the image rectification algorithm is determined from the image data of the view of the reference object calculated in the view generation algorithm and from the OCT scanning data obtained in relation to the reference object, said image rectification algorithm determining a rectification mapping which maps points of an image representation of the reference object in the OCT scanning data onto points of a generated view of the reference object which is based on image data calculated in relation to a view of a reference object arranged in the section of the patient's eye from geometry data about the reference object and which are fed to the view generation algorithm.

8. The computer-implemented method as claimed in claim 7, wherein the view generation algorithm generates a view of the reference object which corresponds to the image representation of the reference object in the OCT scanning data obtained in relation to the reference object.

9. The computer-implemented method as claimed in claim 7, wherein the view generation algorithm uses an image processing method and/or machine learning method in order to ascertain the geometry data in relation to the reference object and/or in order to generate the view of the reference object from the geometry data, and/or
wherein the view generation algorithm uses data relating to the position and location of the reference object in the section of the patient's eye for generating the view of the reference object, which are generated by a measurement method or by a control unit for automatically controlling the reference object, and/or
wherein the view generation algorithm ascertains geometry data of the reference object by virtue of capturing OCT scanning data of the reference object in various recording positions outside of the section of the patient's eye and the geometry data of the reference object being ascertained from these OCT scanning data by means of a 3D reconstruction method.

10. The computer-implemented method as claimed in claim 7, wherein the image rectification algorithm determines a rectification mapping from the OCT scanning data captured by scanning the section of the patient's eye to the visualization data.

11. The computer-implemented method as claimed in claim 10, wherein the rectification mapping of the image rectification algorithm is determined
by virtue of ascertaining a mapping of the view of the reference object generated in the view generation algorithm onto the image representation of the reference object in the OCT scanning data obtained in relation to the reference object; and
by virtue of the ascertained mapping being extended to points of the captured OCT scanning data of the section of the patient's eye outside of the reference object by means of extrapolation.

12. The computer-implemented method as claimed in claim 7, wherein the image rectification algorithm only rectifies a portion of the captured OCT scanning data, in particular the OCT scanning data in the vicinity of the reference object, and leaves the remaining OCT scanning data unchanged.

13. A method for providing visualization data for visualizing at least one section of a patient's eye, wherein a reference object is moved through a plurality of partial sections of the section of the patient's eye and visualization data are determined in the captured OCT scanning data in relation to each of these partial sections using a computer-implemented method as claimed in claim 7.

14. A method for providing visualization data for visualizing at least one section of a patient's eye, wherein the visualization data are redetermined at intervals and/or depending on an event in the section of the patient's eye and/or following the user request, using a computer-implemented method as claimed in claim 7.

15. A computer program product comprising a computer program having program code for carrying out all method steps which are specified in claim 7 when the computer program is loaded on a computer unit and/or executed on a computer unit.

16. A method for providing visualization data for visualizing at least one section of a patient's eye, wherein the visualization data are redetermined at intervals and/or depending on an event in the section of the patient's eye and/or following the user request, using a method as claimed in claim 13.

* * * * *